| United States Patent [19] | [11] 4,020,064 |
|---|---|
| Wade et al. | [45] Apr. 26, 1977 |

[54] 3-[SUBSTITUTED-2-(METHYLAMINO) PHENYL]-4-[2-OXO-2-(HETERO-CYCLIC) ETHYL]-5-SUBSTITUTED-1,2,4-TRIAZOLES

[75] Inventors: Peter C. Wade, Pennington, N.J.; Berthold Richard Vogt, Yardley, Pa.

[73] Assignee: E. R. Squibb & Sons, Inc., Princeton, N.J.

[22] Filed: Apr. 26, 1976

[21] Appl. No.: 680,315

Related U.S. Application Data

[62] Division of Ser. No. 582,549, May 30, 1975, Pat. No. 3,969,366.

[52] U.S. Cl. .................. 260/247.5 E; 260/246 B; 260/247.1 M
[51] Int. Cl.² .............................. C07D 413/02
[58] Field of Search .............. 260/247.5 E, 246 B, 260/247.1 M

[56] References Cited

UNITED STATES PATENTS 3,969,366  7/1976  Wade et al. .............. 260/308 R

*Primary Examiner*—John D. Randolph
*Assistant Examiner*—R. W. Ramsuer

*Attorney, Agent, or Firm*—Lawrence S. Levinson; Merle J. Smith; Stephen B. Davis

[57] ABSTRACT

Compounds of the following formula and their pharmaceutically acceptable salts

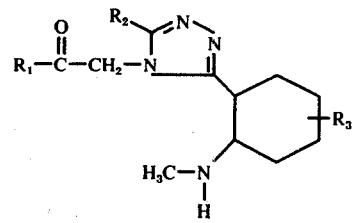

wherein $R_1$ and $R_4$ are the same or different and are each a five or six membered N containing heterocycle attached at an available N atom; $R_2$ is hydrogen, alkyl, trifluoromethyl, phenyl, benzyl, $-(CH_2)_n-R_4$ or $-(CH_2)_n-N(alkyl)_2$; $R_3$ is hydrogen, halogen, nitro, trifluoromethyl, alkyl, alkoxy, or alkylthio; and $n$ is an integer from 1 to 4; are disclosed. These compounds are useful as anti-inflammatory agents.

6 Claims, No Drawings

3-[SUBSTITUTED-2-(METHYLAMINO)PHENYL]-4-[2-OXO-2-(HETERO-CYCLIC)ETHYL]-5-SUBSTITUTED-1,2,4-TRIAZOLES

This application is a division of Ser. No. 582,549 filed on May 30, 1975 now U.S. Pat. 3,969,366.

Summary of the Invention

Compounds having the structure:

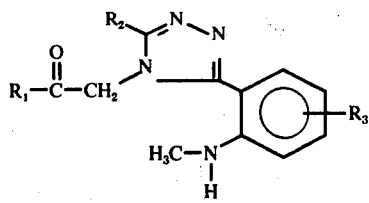

and the pharmaceutically acceptable salts thereof are useful as anti-inflammatory agents. In formula I, and throughout the specification, the symbols have the following meaning:

$R_1$ and $R_4$ are the same or different and are each a five or six membered N containing heterocycle attached at an available N atom.

$R_2$ is hydrogen, alkyl, trifluoromethyl, phenyl, benzyl,

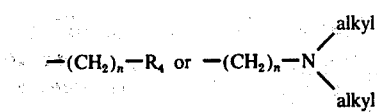

$n$ is an integer from one to four.

The term alkyl, as used throughout the specification, either by itself or as part of a larger group, i.e. alkylthio, refers to both straight and branched chain alkyl group containing 1 to 4 carbon atoms, i.e. methyl, ethyl, n-propyl, t-butyl, etc.

The terms alkoxy and alkylthio, as used throughout the specification, refer to groups of the formulae alkyl-O-and alkyl-S- respectively, wherein alkyl is as defined above.

The term halogen, as used throughout the specification, refers to fluorine, chlorine, bromine and iodine.

The term N containing heterocycle, as used throughout the specification, refers to ring systems having the formula

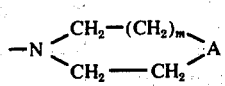

wherein $m$ is 0 or 1 and a is CH—Q, N—Q or oxygen, and Q is hydrogen or alkyl, provided that when $m$ is 0, A is CH—Q, i.e. 1-pyrrolidinyl, 1-piperidinyl, 4-morpholinyl, 1-piperazinyl, 4-alkyl-1-piperazinyl, 4-alkyl-1-piperidinyl and 3-alkyl-1-pyrrolidinyl.

DETAILED DESCRIPTION OF THE INVENTION

The novel compounds of this invention are prepared from compounds having the formula:

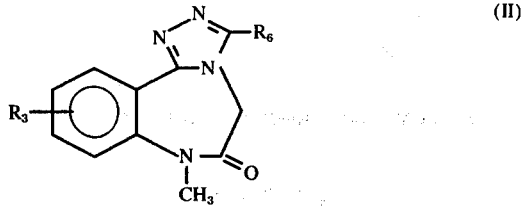

wherein $R_3$ is as defined previously and $R_6$ is hydrogen, alkyl, haloalkyl, trifluoromethyl, phenyl, benzyl, $—(CH_2)_n—N(alkyl)_2$, or $—(CH_2)_n—R_4$, and $R_4$ and $n$ are as defined previously. The compounds of formula II are diclosed in copending application Ser. No. 538,975 filed January 6, 1975.

The compounds of formula I wherein $R_2$ is hydrogen, alkyl, trifluoromethyl, phenyl, benzyl or $—(CH_2)_n—N(alkyl)_2$ are prepared by reacting the appropriate compound of formula II (i.e. $R_6$ is hydrogen, alkyl, trifluoromethyl, phenyl, benzyl or $—(CH_2)_n$-N(alkyl)$_2$) with an excess of an amine of the formula $H—R_1$ wherein $R_1$ is as defined above. This reaction is performed at an elevated temperature for from several minutes to several days, preferably at reflux temperature for from about 1 hour to about 3 days. The reaction can be run neat with the amine also functioning as solvent for the reaction or can be performed in the presence of an inert solvent.

The compounds of formula I wherein $R_2$ is $—(CH_2)_n—R_4$ and $R_4$ and $R_1$ are the same can be prepared by reacting a compound of formula II wherein $R_6$ is $—(CH_2)_n—R_1$ or haloalkyl with an excess of the amine of the formula $H—R_1$. This reaction is performed at an elevated temperature for from several minutes to several days, preferably at reflux temperature for from about 1 hour to about 3 days. The reaction can be run neat with the amine also functioning as solvent for the reaction or can be performed in the presence of an inert solvent.

The compounds of formula I wherein $R_2$ is $—(CH_2)_n—R_4$ and $R_4$ and $R_1$ are different are prepared by reacting a compound of formula II wherein $R_6$ is $—(CH_2)_n—R_4$ with an excess of the amine of the formula $H—R_1$. This reaction is performed at an elevated temperature for from several minutes to several days, preferably at reflux temperature for from about 1 hour to about 3 days. The reaction can be run neat with the amine also functioning as solvent for the reaction or can be performed in the presence of an inert solvent.

As set forth in Ser. No. 538,975 the compounds of formula II wherein $R_6$ is hydrogen, alkyl, phenyl or benzyl are prepared by reacting a compound of the formula

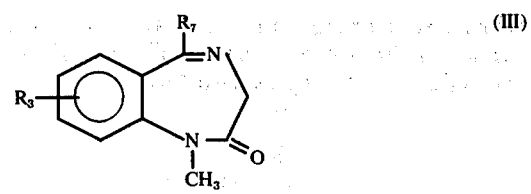

wherein $R_7$ is halogen (preferably bromine or chlorine), sulfhydryl, alkoxy, alkylthio, or phenyl-alkylthio, with an acyl hydrazine having the structure

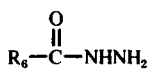

to yield compounds having the structure

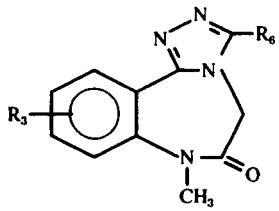

The above reaction can be run in an organic solvent at elevated temperatures, e.g. in benzene under reflux conditions.

The compounds of formula II wherein $R_6$ is haloalkyl or trifluoromethyl are prepared by first reacting a banzodiazepine of formula III with an alkyl carbazate

to obtain a compound having the structure

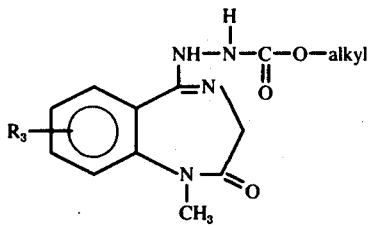

The preferred alkyl carbazate is t-butyl carbazate. The reaction can be run neat, or in a non-reacting organic solvent at a temperature of from about 50° C to about 250° C for from about 5 minutes to about 24 hours, preferably from about 80° C to about 140° C for from about 30 minutes to about 6 hours.

Reaction of the compound of formula VI with either an ester of the formula

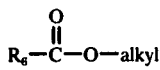 (VII)

or an anhydride of the formula

(VIII)

yields the compound of formula II wherein $R_6$ is haloalkyl or trifluoromethyl. This reaction is run in the presence of an acid having the structure

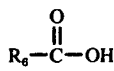 (IX)

or with a mineral acid such as hydrochloric acid, at an elevated temperature, i.e. about 50° C to about 200° C. Alternatively, a compound of formula VI can be pretreated with an acid and then reacted with a compound formula VII or VIII.

The compounds of formula II wherein $R_6$ is

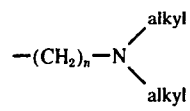

are prepared by reacting the compound of formula II wherein $R_6$ is haloalkyl with an amine of the formula

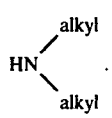

The compounds of formula II wherein $R_6$ is —$(CH_2)_n$—$R_4$ are prepared by reacting the compound of formula II wherein $R_6$ is haloalkyl with an amine of the formula $H$—$R_4$.

The compounds of formula I can be converted into pharmaceutically acceptable acid-addition salts using procedures well known in the art. Illustrative acid-addition salts are the hydrohalides, especially the hydrochloride and hydrobromide which are preferred, sulfate, nitrate, phosphate, tartrate, maleate, fumarate, citrate, succinate, methanesulfonate, benzenesulfonte, toluenesulfonate, and the like.

Preferred compounds of this invention are those of formula I wherein:

$R_1$ and $R_4$ are independently selected from 1-pyrrolidinyl, 1-piperidinyl, 4-morpholinyl, 1-piperazinyl, 4-methyl-1-piperazinyl, 4-methyl-1-piperidinyl, and 3-methyl-1-pyrrolidinyl.

$R_2$ is hydrogen, alkyl of 1–4 carbons, trifluoromethyl, phenyl, or —$(CH_2)_n$—$R_4$ wherein $n$ is 1 to 4.

$R_3$ is hydrogen, chloro, bromo, methyl, or methoxy, especially chloro.

The compounds of formula I, including their pharmaceutically acceptable acid-addition salts, are useful in treating inflammation in mammalian species, e.g., rats, dogs, cats, monkeys, etc. Joint tenderness and stiffness (in conditions such as rheumatoid arthritis) can be treated with the above described compounds.

The compounds of this invention can be formulated for use as amnti-inflammatory agents according to accepted pharmaceutical practice in oral dosage forms such as tablets, capsules, elixirs, or powders, or in an injectable form in a sterile aqueous vehicle prepared according to conventional pharmaceutical practice. The compounds of this invention may be administered in amounts of 100 mg/70 kg/day to 2 g/70 kg/day, preferably 100 mg/70 kg/day to 1 g/70 kg/day.

The following examples are specific embodiments of this invention. All temperatures are expressed in degrees centigrade.

EXAMPLE 1

3-[5-Chloro-2-(methylamino)phenyl]-4-[2-oxo-2-(1-pyrrolidinyl)-ethyl-5-(trifluoromethyl)-1,2,4-triazole, hydrochloride (1:1)

(a) 10-chloro-7-methyl-3-(trifluoromethyl)-5*H*-s-triazolo[4,3-*d*]-[1,4]benzodiazepin-6(7*H*)-one 5,7-Dichloro-1-methyl-1,4-benzodiazepine-2 (7.5 g.) and *t*-butylcarbazate (7.9 g.) are refluxed in 300 ml. of benzene for 90 minutes. The solvent is removed under vacuum and 20 ml. of trifluoroacetic acid is added. The mixture is stirred at room temperature for 30 minutes. The trifluoroacetic acid is removed under vacuum and 30 ml. of trifluoroacetic anhydride are added. The resulting solution is refluxed for 2 hours followed by evaporation of the volatiles. The residue is stirred with 250 ml. of ether to yeild 6.9 g. of a fine powder which after recrystallization from methanol and drying under vacuum at 130° C for 3 hours, has a melting point 186°–187°.

(b) 3-[5-Chloro-2-(methylamino)phenyl]-4-[2-oxo-2-(1-pyrrolidinyl)-ethyl]-5-(trifluoromethyl)-1,2,4-triazole, hydrochloride (1:1)

4.8 g. (0.0152 mole) of 10-chloro-7-methyl-3-(trifluoromethyl)-5H-s-triazolo[4,3-d] [1,4] benzodiazepin-6(7H)-one from part (a) is dissolved in 40 ml. of pyrrolidine and the resulting solution is refluxed for 1 hour. The pyrrolidine is removed under vacuum, 3N aqueous NaOH is added, and the mixture is extracted several times with benzene. The benzene solutions are combined, dried over Na$_2$SO$_4$, decanted from the drying agent, and the solvent removed under vacuum to leave 5.64 g. of an orange-yellow gum. This gum is dissolved in ether and one equivalent of ethereal HCl is added. The resulting precipitate is filtered off, dissolved in ethanol and reprecipitated with ether to yield 4.4 g. of 3-[5-chloro-2-(methylamino)phenyl]-4-[2-oxo-2-(1-pyrrolidinyl)ethyl]-5-(trifluoromethyl)-1,2,4-triazole, hydrochloride (1:1); m.p. 161°–162.5°.

EXAMPLE 2

3-[5-Chloro-2-(methylamino)phenyl]-4-[2-oxo-2-(4-morpholinyl)ethyl]-5-(trifluoromethyl)-1,2,4-triazole 4.8 g. (0.0152 mole) of 10-chloro-7-methyl-3-(trifluoromethyl)-5H-s-triazolo[4,3-d] [1,4] benzodiazepin-6(7H)-one from example 1a are dissolved in 40 ml. of morpholine and the resulting solution is refluxed for 3 days. The morpholine is removed under vacuum, 3N aqueous NaOH is added, and the mixture is extracted with benzene. The benzene solution is dried over Na$_2$SO$_4$, decanted from drying agent, and the solvent removed under vacuum to yield a gum. This gum is chromatographed on silica gel plates with chloroform/ethyl acetate, 6:4. The largest band is isolated, extracted with chloroform, the chloroform is evaporated, and the residue is recrystallized from ethanol to yield 3-[5-chloro-2-(methylamino)phenyl]-4-[2-oxo-2-(4-morpholinyl)ethyl]-5-(trifluoromethyl)-1,2,4-triazole; m.p. 152°–153°.

EXAMPLE 3

3-[5-Chloro-2-(methylamino)phenyl]-4-[2-oxo-2-(1-pyrrolidinyl)-ethyl]-5-methyl-1,2,4-triazole, hydrochloride (1:1)

(a) 10-Chloro-3,7-dimethyl-5H-s-triazola[4,3-d]benzodiazepin-6(7H)-one 5,7-Dichloro-1-methyl-1,4-benzodiazepinione-2 (4.86 g.) and acethydrazide (5.02 g.) are refluxed together for 14 hours in benzene (300 ml.). The solvent is removed under vacuum and the residue is dissolved in hot water. On cooling, 4.2 g. of white needles precipitate and are filtered off. They are recrystallized from water containing about 25% methanol. The needles are dried at 150° C under vacuum overnight. The drying process yields the title compound as a powder, melting point 228.5°–229.5°.

(b) 3-[5-Chloro-2-(methylamino)phenyl-4-[2-oxo-2-(1-pyrrolidinyl)-ethyl]-5-methy-1,2,4-triazole, hydrochloride (1:1)

Following the procedure of example 1b but substituting an equivalent amount of 10-chloro-3,7-dimethyl-5H-s-triazolo[4,3-d] [1,4]benzodiazepin-6(7H)-one for the 10-chloro-7-methyl-3-(trifluoromethyl)-5H-s-triazolo[4,3-d][1,4]benzodiazepin-6(7H)-one one obtains the titled compound.

EXAMPLE 4

3-[5-Chloro-2-(methylamino)phenyl]-4-[2-oxo-2-(1-pyrrolidinyl)-ethyl]-5-phenyl-1,2,4-triazole, hydrochloride (1:1)

(a) 10-Chloro-7-methyl-3-phenyl-5H-s-triazolo[4,3-d][1,4]benzodiazepin-6(7H)-one 5,7-Dichloro-1-methyl-1,4-benzodiazepinone-2 (2.79 g.) and benzoylhydrazide (2.86 g.) are refluxed in 150 ml. of benzene for 3 hours. The solid material is fitered from the hot reaction mixture and the solvent removed from the filtrate under vacuum. The residue is recrystallized twice from methanol and dried at 125° C under vacuum for 3 hours to yield 2.9 g. of the title compound, melting point 204.5°–205.5°.

(b) 3-[5-Chloro-2-(methylamino)phenyl]-4-[2-oxo-2-(2-pyrrolidinyl)-ethyl]-5-phenyl-1,2,4-triazole, hydrochloride (1:1)

Following the procedure of example 1b but substituting an equivalent amount of 10-chloro-7-methyl-3-phenyl-5H-s-triazolo[4,3-d][1,4]benzodiazepin-6(7H)-one for the 10-chloro-7-methyl-3-(trifluoromethyl)-5H-s-triazolo[4,3d][1,4]benzodiazepin-6(7H)-one, one obtains the titled compound.

EXAMPLE 5

3-[5-Chloro-2-(methylamino)phenyl]-4-[2-oxo-2-(1-pyrrolidinyl)-ethyl]-1,2,4-triazole, hydrochloride (1:1)

(a) 10-Chloro-7-methyl-5H-s-triazolo[4,3-d][1,4]benzodiazepin-6(7H)-one 5,7-Dichloro-1-methyl-1,4-benzodiazepinone-2 (14.6 g.) and formylhydrazide (12 g.) are refluxed in 300 ml. of benzene for 3 hours. The solvent is decanted from the resulting precipitate which is recrystallized twice from 95% ethanol to yield 7.5 g. of the title compound. An additional 5 g. of the title compound can be obtained from the decanted solvent. The title compound has a melting point of 272°–274°.

(b) 3-[5-Chloro-2-(methylamino)phenyl]-4-[2-oxo-2-(1-pyrrolidinyl)-ethyl]-1,2,4-triazole, hydrochloride (1:1)

Following the procedure of example 1b but substituting an equivalent amount of 10-chloro-7-methyl-5H-s-triazolo[4,3-d]-[1,4]benzodiazepin-6(7H)-one for the 10-chloro-7-methyl-3-(trifluoromethyl)-5H-s-triazolo[4,3-d][1,4]benzodiazepin-6(7H)-one, one obtains the titled compound.

EXAMPLE 6

3-[5-Chloro-2-(methylamino)phenyl]-4-[2-oxo-2-(1-pyrrolidinyl)-ethyl]-5-(4-methyl-1-piperazinylmethyl)-1,2,4-triazole, hydrochloride (1:1)

(a) 10-Chloro-3-(chloromethyl)-7-methyl-5H-s-triazolo[4,3-d][1,4]-benzodiazepin-6(7H)-one 5,7-Dichloro-1-methyl-1,4-benzodiazepinone-2 (2.43 g.) and t-butylcarbazate (2.64 g.) are refluxed in 125 ml. of benzene for 90 minutes. The solvent is removed under vacuum and 9 g. of chloroacetic acid is added to the residue. After heating the mixture at 80° for 45 minutes, 7.5 g. of chloroacetic anhydride is added and heating is continued at 90° C for an additional 3 hours. The mixture is crystallized from water to give 1.5 g. of a solid which is dried overnight at 110° under vacuum to yield the title compound, melting point 193°–194.5°

(b) 10-Chloro-7-methyl-3-(4-methyl-1-piperazinyl-methyl)-5H-s-triazolo[4,3-d][1,4]benzodiazepin-6(7H)-one 5 g. of 10-chloro-3-(chloromethyl)-7-methyl-5H-s-triazolo[4,3-d][1,4]benzodiazepin-6(7H)-one from part (a) is suspended in 50 ml. of 1,2-dimethoxyethane. N-methylpiperazine (5.4 g.) is added to the suspension and the mixture is heated under reflux for 5 hours. The solvent is stripped off, 3N aqueous sodium hydroxide is added to the residue and the mixture is extracted with several portions of chloroform. The combined chloroform extracts are dried over sodium sulfate and the solvent is removed under vacuum to leave a residue which is recrystallized from absolute ethanol to yield 4 g. of the title compound, melting point 228.5°–230.5°.

(c) 3-[5-Chloro-2-(methylamino)phenyl]-4-[2-oxo-2-(1-pyrrolidinyl)-ethyl]-54-methyl-1-piperazinylmethyl)-1,2,4-triazole, hydrochloride (1:1)

Following the procedure of example 1b but substituting an equivalent amount of 10-chloro-7-methyl-3-(4-methyl-1-piperazinylmethyl)-5H-s-triazolo[4,3-d][1,4]benzodiazepin-6(7H)-one for the 10-chloro-7-methyl-3-(trifluoromethyl)-5H-s-triazolo-[4,3-d][1,4]benzodiazepin-6(7H)-one, one obtains the titled compound.

EXAMPLES 7–29

Following the procedure of example 1b but substituting an equivalent amount of the triazolo[4,3-d][1,4]benzodiazepin-6(7H)-one shown below in column I for the 10-chloro-7-methyl-3-(trifluoromethyl)-5H-s-triazolo[4,3-d][1,4]benzodiazepin-6(7H)-one, one obtains the products shown below in column II.

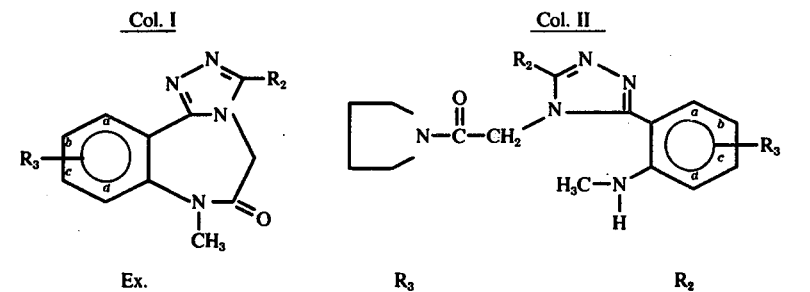

| Ex. | a | b | c | d | $R_2$ |
|---|---|---|---|---|---|
| 7 | F | H | H | H | $CF_3$ |
| 8 | H | H | Cl | H | $CH_3$ |
| 9 | H | H | H | Cl | $C_2H_5$ |
| 10 | H | Br | H | H | H |
| 11 | H | $CF_3$ | H | H | n—$C_3H_7$ |
| 12 | H | H | $CF_3$ | H | —⟨phenyl⟩ |
| 13 | H | Cl | H | H | —$CH_2$—⟨phenyl⟩ |
| 14 | H | H | $CH_3$ | H | $CF_3$ |
| 15 | $C_2H_5$ | H | H | H | $CH_3$ |
| 16 | H | $NO_2$ | H | H | $CF_3$ |
| 17 | H | H | H | $NO_2$ | t—$C_4H_9$ |
| 18 | H | $OCH_3$ | H | H | —⟨phenyl⟩ |
| 19 | H | H | H | $OCH_3$ | $CH_2$—⟨phenyl⟩ |
| 20 | H | I | H | H | H |
| 21 | Cl | H | H | H | $CF_3$ |
| 22 | H | H | H | H | —$CH_2$—N(CH$_3$)$_2$ |
| 23 | H | Cl | H | H | —(CH$_2$)$_3$—N(CH$_3$)$_2$ |
| 24 | H | Br | H | H | —(CH$_2$)$_2$—N(CH$_3$)(C$_2$H$_5$) |
| 25 | H | H | Cl | H | —CH$_2$—N(morpholino) |

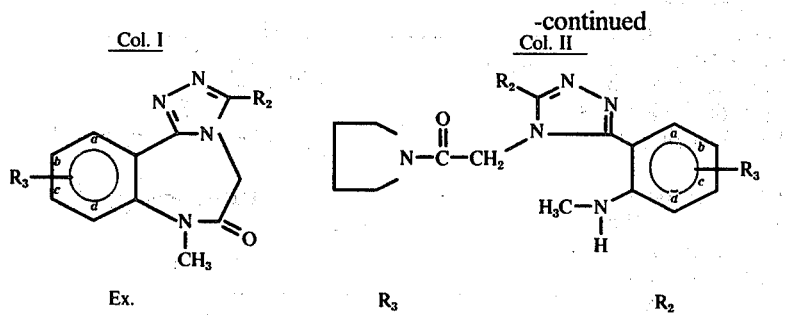

| Ex. | R₃ | | | | R₂ |
|---|---|---|---|---|---|
| | a | b | c | d | |
| 26 | H | Cl | H | H | —(CH₂)₂—N⟨piperazinyl⟩N—H |
| 27 | H | H | CH₃ | H | —(CH₂)₃—N⟨pyrrolidinyl⟩ |
| 28 | H | H | H | H | —(CH₂)₄—N⟨piperazinyl⟩N—CH₃ |
| 29 | H | H | Br | H | —CH₂—N⟨aziridinyl-CH₃⟩ |

EXAMPLES 30–36

Following the procedure of example 1b but substituting for the pyrrrolidine the amines listed below in column I one obtains the products listed below in column II.

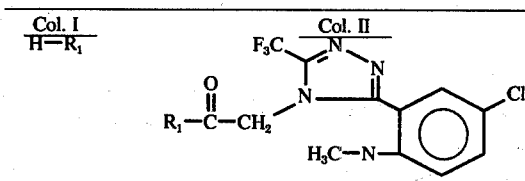

| Ex. | R₁ |
|---|---|
| 30 | —N⟨piperazinyl⟩NH |
| 31 | —N⟨piperazinyl⟩N—CH₃ |
| 32 | —N⟨piperazinyl⟩N—C₃H₇ |
| 33 | piperidinyl (N at ring) |
| 34 | —N⟨pyrrolidinyl-CH₃⟩ |
| 35 | —N⟨pyrrolidinyl-C₂H₅⟩ |
| 36 | —N⟨piperidinyl-CH₃⟩ |

Similarly, by employing the amines of Col. I of examples 30–36 in place of the pyrrolidine in the procedure of examples 3–29, other compounds within the scope of the invention are obtained.

EXAMPLE 37

3-[5-Chloro-2-(methylamino)phenyl]-4-[2-oxo-2-(1-pyrrolidinyl)-ethyl]-5-(1-pyrrolidinylmethyl)-1,2,4-triazole, hydrochloride (1:1)

5 g. (0.0168 mole) of 10-chloro-3-(chloromethyl)-7-methyl-5H-s-triazolo[4,3-d][1,4]benzodiazepin-6(7H)-one from example 6b are dissolved in 40 ml. of pyrrolidine and the resulting solution is refluxed for one hour and allowed to stand overnight at 25°. The precipitate that forms is removed by filtration to give 3.1 g. of white powdery product. The pyrrolidine is removed under vacuum from the filtrate and the residue is stirred with 3n aqueous NaOH and benzene. The aqueous solution is extracted twice more with benzene, the organic solutions are combined and dried over $Na_2SO_4$. The solvent is decanted from the drying agent and the solvent removed under vacuum to yield an additional 3.2 g. of 3-[5-chloro-2-(methylamino)-phenyl]-4-[2-oxo-2-(1-pyrrolidinyl)ethyl]-5-(1-pyrrolidinylmethyl)-1,2,4-triazole.

3 g. of this free base is neutralized in methanol-ethanol (1:1) with one equivalent of ethereal HCl. The salt precipitates with ether to yield 2.8 g. 3-[5-chloro-2-(methylamino)phenyl]-4-[2-oxo-2-(1-pyrrolidinyl)ethyl]5-(1-pyrrolidinylmethyl)-1,2,4-triazole, hydrochloride (1:1), m.p. 247°–248.5°.

EXAMPLES 38–45

Following the procedure of example 37 but substituting an equivalent amount of triazolo[4,3-d][1,4]benzodiazepin-6(7H)-one shown below in column I for the 10-chloro-7-methyl-3-(chloromethyl)-5H-s-triazolo[4,3-d][1,4]benzodiazepin-6(7H)-one, one obtains the products shown below in column II.

EXAMPLES 46–52

Following the procedure of example 37 but substituting for the pyrrolidine the amines listed below in column I one obtains the products listed below in column II.

| Ex. | Col. I $R_1$ |
|---|---|
| 46 | piperazinyl (N—H) |
| 47 | 4-methylpiperazinyl (N—CH₃) |
| 48 | 4-ethylpiperazinyl (N—C₂H₅) |
| 49 | piperidinyl |

| Ex. | $R_3$ (a, b, c, d) | | | | $R_6$ | $R_2$ |
|---|---|---|---|---|---|---|
| | a | b | c | d | | |
| 38 | H | H | H | H | —CH₂Cl | —CH₂—N(pyrrolidinyl) |
| 39 | F | H | H | H | —CH₂Br | —CH₂—N(pyrrolidinyl) |
| 40 | H | H | Cl | H | —(CH₂)₂—Cl | —(CH₂)₂—N(pyrrolidinyl) |
| 41 | H | Br | H | H | —(CH₂)₃—Cl | —(CH₂)₃—N(pyrrolidinyl) |
| 42 | H | H | H | Cl | —(CH₂)₄—Cl | —(CH₂)₄—N(pyrrolidinyl) |
| 43 | H | C₃H₇ | H | H | —CH₂Cl | —CH₂—N(pyrrolidinyl) |
| 44 | H | H | H | OCH₃ | —(CH₂)₂—Cl | —(CH₂)₂—N(pyrrolidinyl) |
| 45 | H | NO₂ | H | H | —CH₂—Br | —CH₂—N(pyrrolidinyl) |

-continued

| Col. I | Col. II |
|---|---|
| H—R₁ | 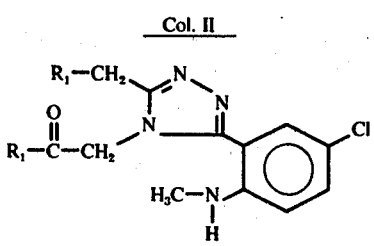 |

| Ex. | R₁ |
|---|---|
| 50 | 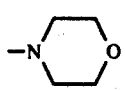 |
| 51 | 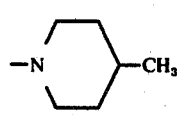 |
| 52 | 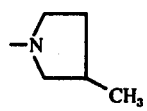 |

Similarly, by employing the amines of Col. I of example 46–52 in place of the pyrrolidine in the procedure of examples 38–45, other compounds within the scope of the invention are obtained.

What is claimed is:

1. A compound of the formula

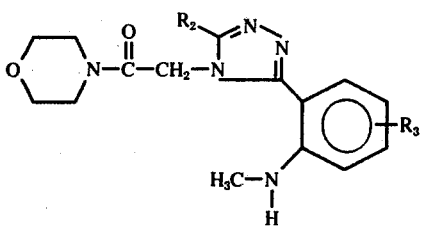

wherein $R_2$ is hydrogen, alkyl of 1 to 4 carbons, trifluoromethyl, phenyl, benzyl,

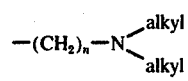

wherein each alkyl is of 1 to 4 carbons or

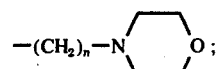

$n$ is an integer from 1 to 4; and $R_3$ is hydrogen, halogen, nitro, trifluoromethyl, alkyl of 1 to 4 carbons, alkoxy of 1 to 4 carbon, or alkylthio of 1 to 4 carbons; and a pharmaceutically acceptable salt thereof.

2. The compound of claim 1 wherein, $R_2$ is hydrogen, alkyl of 1 to 4 carbons, trifluoromethyl or phenyl; and $R_3$ is hydrogen, chloro, bromo, methyl, or methoxy.

3. The compound of claim 2 wherein $R_3$ is chloro.

4. The compound of claim 3, 3-[5-chloro-2-(methylamino)phenyl]-4-[2-oxo-(4-morpholinyl)ethyl]-5-(trifluoromethyl)-1,2,4-triazole.

5. The compound of claim 1 wherein $R_2$ is

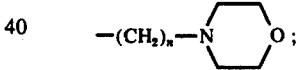

$n$ is an integer from 1 to 4; and $R_3$ is hydrogen, chloro, bromo, methyl or methoxy.

6. The compound of claim 5 wherein $R_3$ is chloro.

* * * * *

UNITED STATES PATENT AND TRADEMARK OFFICE
CERTIFICATE OF CORRECTION

PATENT NO. : 4,020,064
DATED : April 26, 1977
INVENTOR(S) : Peter C. Wade et al.

It is certified that error appears in the above-identified patent and that said Letters Patent are hereby corrected as shown below:

In the title, "Hetero-Cyclic" should read --Heterocyclic--.

In the abstract, the structure should read

-- 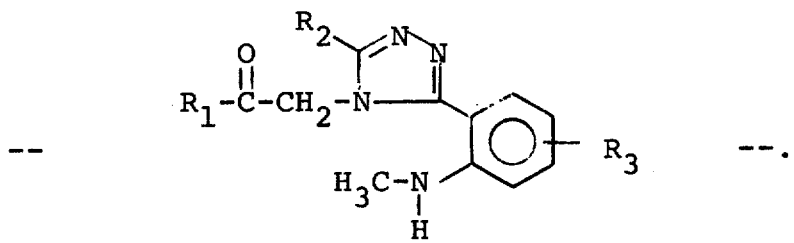 --.

Col. 2, line 16, "diclosed" should read --disclosed--.

Col. 3, line 26, "$\overset{O}{\overset{\|}{C}}$-NHNH$_2$)" should read --alkyl-O-$\overset{O}{\overset{\|}{C}}$-NHNH$_2$)--.

Col. 4, line 29, "benzenesulfonte" should read --benzenesulfonate--.

Col. 5, line 59, "benzodiazepinione" should read --benzodiazepinone--.

Col. 6, line 21, "fitered" should read --filtered--.

Col. 6, line 27, "(2-pyrrolidinyl)" should read --(1-pyrrolidinyl)--.

Col. 6, line 33, "[4,3d]" should read --[4,3-d]--.

Col. 8, line 1, "siolvent" should read --solvent--.

Col. 8, line 5, "54-methyl" should read --5-(4-methyl--.

UNITED STATES PATENT AND TRADEMARK OFFICE
CERTIFICATE OF CORRECTION

PATENT NO. : 4,020,064
DATED : April 26, 1977
INVENTOR(S) : Peter C. Wade et al.

It is certified that error appears in the above-identified patent and that said Letters Patent are hereby corrected as shown below:

Col. 10, line 68, "3n" should read --3N--.

Col. 11, line 12, "thyl]5" should read --thyl]-5--.

Col. 13, lines 38 and 40, "example" should read --examples--.

Col. 14, line 28, "carbon" should read --carbons--.

Col. 3, line 22, "ban-" should read --ben- --.

Signed and Sealed this nineteenth Day of July 1977

[SEAL]

Attest:

RUTH C. MASON
Attesting Officer

C. MARSHALL DANN
Commissioner of Patents and Trademarks